(12) United States Patent
Chang et al.

(10) Patent No.: US 9,091,647 B2
(45) Date of Patent: Jul. 28, 2015

(54) DIRECT SENSING BIOFETS AND METHODS OF MANUFACTURE

(75) Inventors: Yi-Hsien Chang, Shetou Township (TW); Chun-Ren Cheng, Hsin-Chu (TW); Shih-Wei Lin, Taipei (TW); Yi-Shao Liu, Zhubei (TW)

(73) Assignee: Taiwan Semiconductor Manufacturing Company, Ltd.

( * ) Notice: Subject to any disclaimer, the term of this patent is extended or adjusted under 35 U.S.C. 154(b) by 193 days.

(21) Appl. No.: 13/607,720

(22) Filed: Sep. 8, 2012

(65) Prior Publication Data

US 2014/0073039 A1    Mar. 13, 2014

(51) Int. Cl.
*G01N 27/00* (2006.01)
*H01L 21/00* (2006.01)
*G01N 27/414* (2006.01)
*H01L 27/28* (2006.01)

(52) U.S. Cl.
CPC .......... *G01N 27/4145* (2013.01); *H01L 27/283* (2013.01)

(58) Field of Classification Search
USPC .......... 422/50, 68.1, 82, 82.01; 438/1, 48, 49, 438/142–308
See application file for complete search history.

(56) References Cited

U.S. PATENT DOCUMENTS

2006/0197118 A1* 9/2006 Migliorato et al. ........... 257/253
2010/0283087 A1* 11/2010 Lehmann et al. ............. 257/253

OTHER PUBLICATIONS

Wen-Yaw Chung ; Chung-Huang Yang ; Ming-Ga Wang; ISFET-based sensor signal processor chip design for environment monitoring applications. Proc. SPIE 5586, Advanced Environmental, Chemical, and Biological Sensing Technologies II, 18 (Dec. 7, 2004); doi:10.1117/12.572324.*

* cited by examiner

*Primary Examiner* — Paul Hyun
*Assistant Examiner* — Robert Eom
(74) *Attorney, Agent, or Firm* — Slater & Matsil, L.L.P.

(57) ABSTRACT

The present disclosure provides a biological field effect transistor (BioFET) and a method of fabricating a BioFET device. The method includes forming a BioFET using one or more process steps compatible with or typical to a complementary metal-oxide-semiconductor (CMOS) process. The BioFET device includes a plurality of micro wells having a sensing gate bottom and a number of stacked well portions. A bottom surface area of a well portion is different from a top surface area of a well portion directly below. The micro wells are formed by multiple etching operations through different materials, including a sacrificial plug, to expose the sensing gate without plasma induced damage.

14 Claims, 13 Drawing Sheets

DIRECT SENSING BIOFETS AND METHODS OF MANUFACTURE

FIELD

This disclosure relates to biosensors and methods for forming biosensors. Particularly, this disclosure relates to biological field-effect-transistors (bioFETs) and methods for forming them.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and MEMS.

BioFETs (biological field-effect transistors, biologically sensitive field-effect transistors, biologically active field-effect transistors, or bio-organic field-effect transistors) are a type of biosensor that includes a transistor for electrically sensing biomolecules or bio-entities. While BioFETs are advantageous in many respects, challenges in their fabrication and/or operation arise, for example, due to compatibility issues between the semiconductor fabrication processes, the biological applications, restrictions and/or limits on the semiconductor fabrication processes, integration of the electrical signals and biological applications, and/or other challenges arising from implementing large scale integration (LSI) process.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

In a biological field-effect transistor (BioFET), the gate of a metal-oxide-semiconductor field-effect transistor (MOSFET), which controls the conductance of the semiconductor between its source and drain contacts, is replaced by a bio- or biochemical-compatible layer or a biofunctionalized layer of immobilized probe molecules that act as surface receptors. Essentially, a BioFET is a field-effect biosensor with a semiconductor transducer. A decided advantage of BioFETs is the prospect of label-free operation. Specifically, BioFETs enable the avoidance of costly and time-consuming labeling operations such as the labeling of an analyte with, for instance, fluorescent or radioactive probes.

A typical detection mechanism for BioFETs is the conductance modulation of the transducer due to the binding of a target biomolecule or bio-entity to a sensing surface or a receptor molecule immobilized on the sensing surface of the BioFET. When the target biomolecule or bio-entity is bonded to the sensing surface or the immobilized receptor, the drain current of the BioFET is varied by the potential from the sensing surface. This change in the drain current can be measured and the bonding of the receptor and the target biomolecule or bio-entity can be identified. A great variety of biomolecules and bio-entities may be used to functionalize the sensing surface of the BioFET such as ions, enzymes, antibodies, ligands, receptors, peptides, oligonucleotides, cells of organs, organisms and pieces of tissue. For instance, to detect ssDNA (single-stranded deoxyribonucleic acid), the sensing surface of the BioFET may be functionalized with immobilized complementary ssDNA strands. Also, to detect various proteins such as tumor markers, the sensing surface of the BioFET may be functionalized with monoclonal antibodies.

One difference in various types of BioFETs is the location of the sensing surface. One example of a sensing surface is a top of a floating gate connected to the gate of the BioFET. The floating gate is connected to the gate structure of the BioFET though a stack of metal interconnect lines and vias (or multi-layer interconnect, MLI). The various metal layers over the gate electrode can also contribute to damage by antenna effect during the MLI formation process. In such a BioFET, the potential-modulating reaction takes place at an outer surface of the final (top) metal layer or a dielectric surface formed on top of the MLI and is sensed indirectly by the BioFET. This embodiment may be disadvantageous however, in that the sensitivity of the device is decreased due to the presence of parasitic capacitances associated with the MLI. As result a minimum sensing plate dimension is usually specified so that a sufficiently detectable amount of potential-modulating reaction can take place. The minimum sensing plate dimension in turn limits the BioFET density.

In other examples of sensing surfaces, the biomolecules bind directly or through receptors on the gate or the gate dielectric of the BioFETs. These BioFETs directly sense the target biomolecules without the parasitic capacitances associated with MLI. Construction of such BioFETs requires removal of the MLI material above the BioFET to form a sensing well and exposing the gate electrode or gate dielectric to the fluidic environment where potential-modulating surface reactions occur. These BioFETs are more sensitive than the floating gate types but are challenging to construct for several reasons. The sensing well etched has a high aspect ratio of, for example, 30 or greater, so it is usually formed with a high energy plasma etch. The high-aspect ratio of the sensing well also limits the profile of the etched sensing well. The high energy plasma etch can damage the gate electrode due to charge-induced damage. One attempt in reducing the aspect ratio of the sensing well to make the etch easier results in a limitation of the number of metal layers, down to one or two metal layers. The reduction in metal layers limits the interconnect routing and integration options of the device, for example, the number and type of circuits for controlling the BioFET. The process is also very sensitive to alignment, because misalignment may expose the metals in the MLI surrounding the sensing well or cause the sensing surface area to be less than designed.

The present disclosure provides BioFETs with a direct sensing surface at the gate or the gate dielectric and methods for making the BioFETs. A multi-tiered micro well is formed over the sensing surface at the gate electrode or the gate dielectric of the BioFET. The methods of making the BioFETs are compatible with the complementary metal-oxide-semiconductor (CMOS) process employing multiple etch processes using different chemistries to form the micro well. As compared to the floating gate indirect sensor type BioFETs, antenna effect type of damage is eliminated or substantially reduced because the gate of the BioFET is not connected to a metal layer and the BioFET density can be made higher without being limited by the minimum sensing plate dimension. The BioFET of the present disclosure, having a multi-tiered micro well, has a bigger process window because the aspect ratio for each etch process is lower and the etch processes used are less sensitive to misalignments as compared with a sensing well not having a multi-tiered structure. The likelihood of charge-induced damage of the gate electrode is also reduced. The process embodiments of the present disclosure also allows an optional replacement of the gate dielectric material at the bottom of the micro well with another gate dielectric material.

Figure 1A:
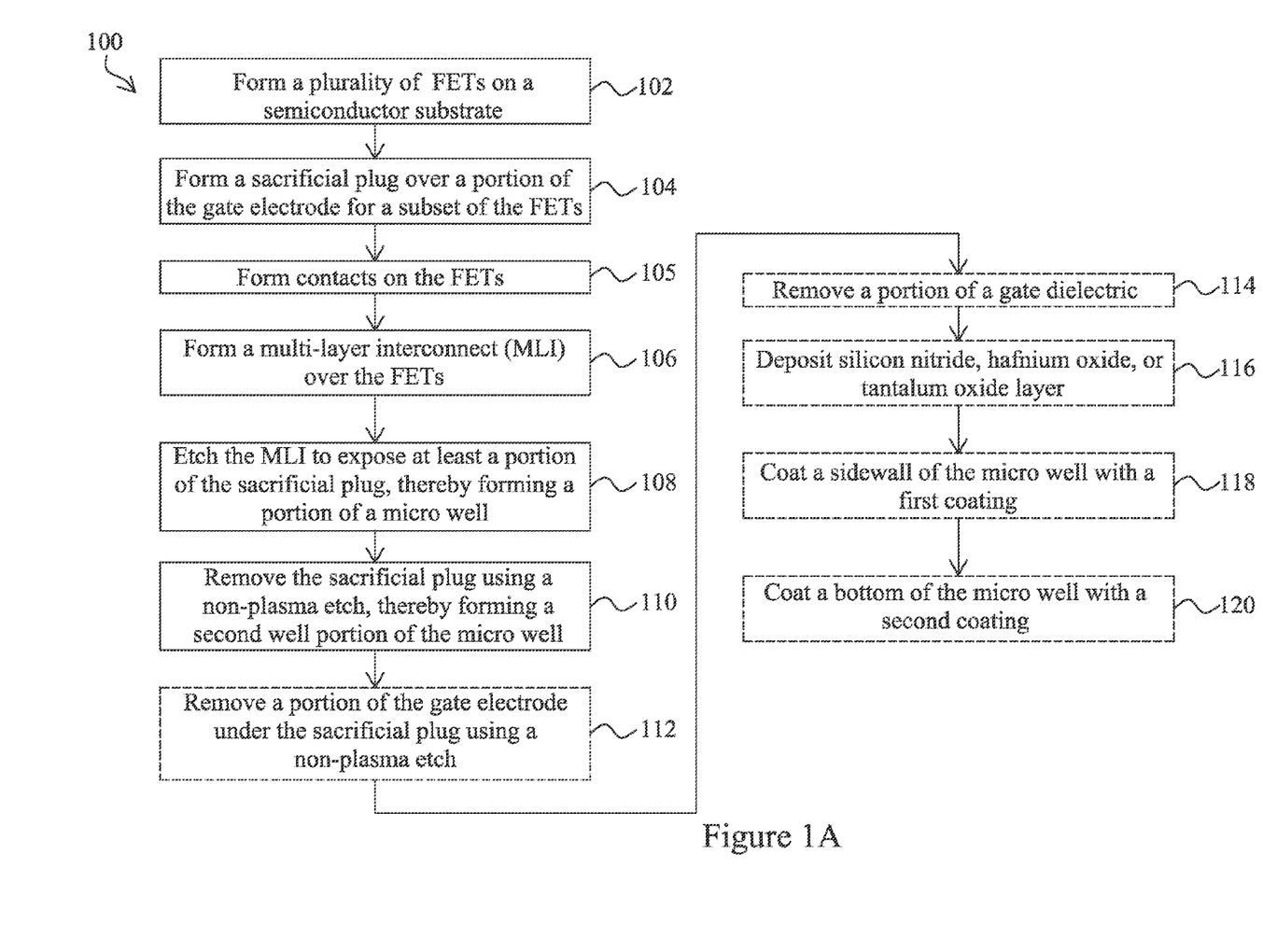
FIG. 1A is a flow chart of an embodiment of a method of fabricating a BioFET device according to one or more aspects of the present disclosure.
Figure 1B:
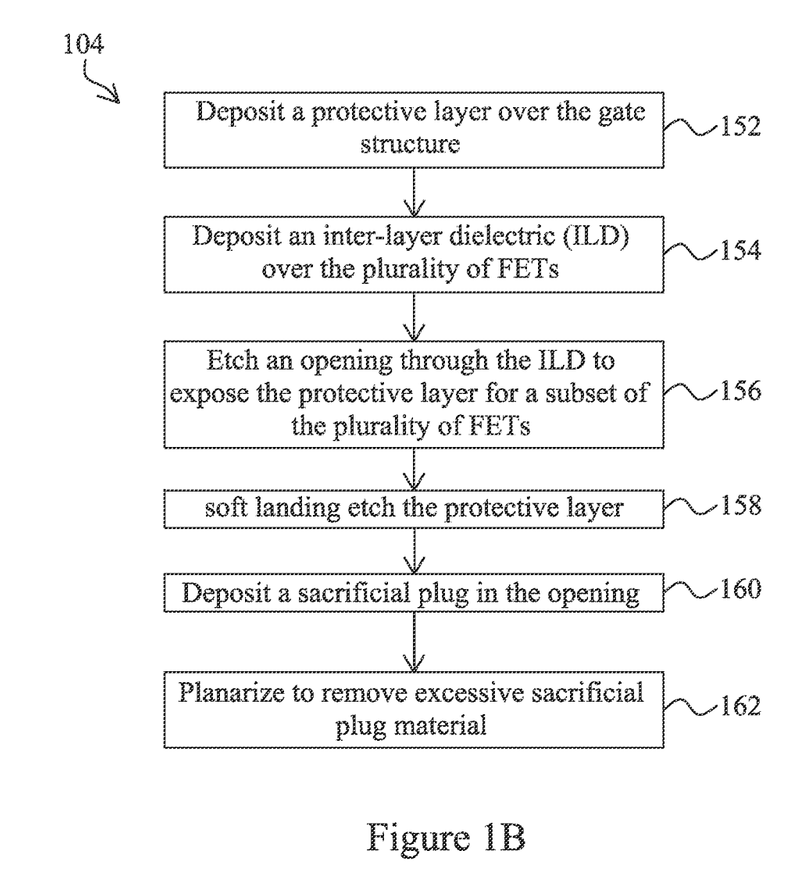
FIG. 1B is a flow chart of an operation of the method embodiment in FIG. 1A according to one or more aspects of the present disclosure.

Illustrated in FIG. 1A is an embodiment of a method 100 of fabricating a bio-organic field effect transistor (BioFET). The method 100 may include forming a BioFET using one or more process steps compatible with or typical to a complementary metal-oxide-semiconductor (CMOS) process. It is understood that additional steps can be provided before, during, and after the method 100, and some of the steps described below can be replaced or eliminated, for some embodiments of the method. Further, it is understood that the method 100 includes steps having features of a typical CMOS technology process flow and some of them are only described briefly herein. It is also noted that FIG. 1B provides further embodiments of the method 100, which may provide additional details applicable to the method 100.

The method 100 begins at block 102 where a plurality of field-effect transistors (FETs) are formed on a semiconductor substrate. The semiconductor substrate may be a silicon substrate. Alternatively, the substrate may include another elementary semiconductor, such as germanium; a compound semiconductor including silicon carbide, gallium arsenic, gallium phosphide, indium phosphide, indium arsenide, and/or indium antimonide; an alloy semiconductor including SiGe, GaAsP, AlInAs, AlGaAs, GaInAs, GaInP, and/or GaInAsP; or combinations thereof. In an embodiment, the substrate is a semiconductor on insulator (SOI) substrate. The SOI substrate may include a buried oxide (BOX) layer formed by a process such as separation by implanted oxygen (SIMOX), and/or other suitable processes. The substrate may include doped regions, such as p-wells and n-wells. In the present disclosure, a wafer is a semiconductor substrate and various features formed in and over the semiconductor substrate. The wafer may be in various stages of fabrication and is processed using the CMOS process.

Figure 2:
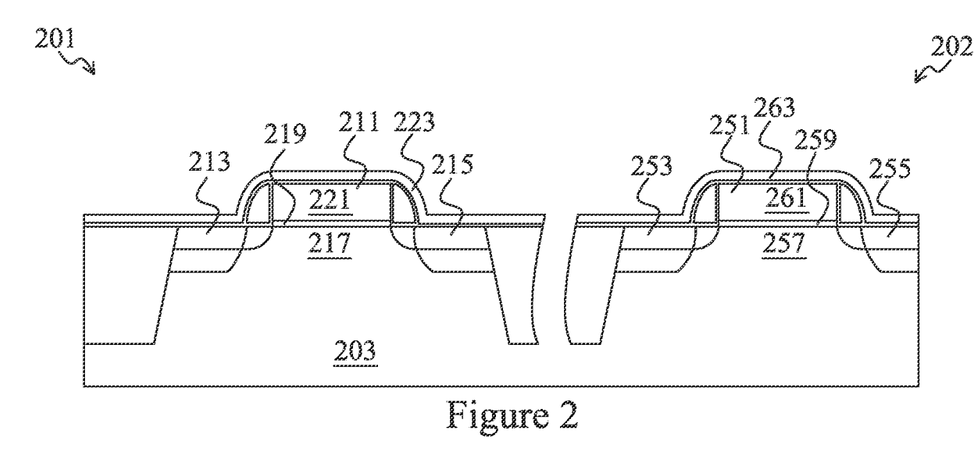
FIGS. 2 and 3 are cross-sectional views of a BioFET device at various intermediate stages of formation according to one or more aspects of the present disclosure.

FIG. 2 is a cross section of FETs 201 and 202 formed on the semiconductor substrate 203. FET 201 is a BioFET; and FET 202 is not a BioFET. The FETs 201 and 202 include gate structures (211/251), source regions (213/253), drain regions (215/255), and channel regions (217/257), respectively, interposing the source regions (213/253) and drain regions (215/255). The source, drain, and/or channel region may be formed on an active region of the semiconductor substrate. The FETs 201 and 202 may be n-type FETs (nFETs) or p-type FETs (pFETs). For example, the source/drain regions may comprise n-type dopants or p-type dopants depending on the FET configuration. The gate structure (211/251) includes a gate dielectric layer (219/259), a gate electrode layer (221/261), and/or other suitable layers. In an embodiment, the gate electrode (221/261) is polysilicon. Other suitable gate electrodes include metal gate electrodes including material such as, Cu, W, Ti, Ta, Cr, Pt, Ag, Au; suitable metallic compounds like TiN, TaN, NiSi, CoSi; combinations thereof; and/or other suitable conductive materials. The gate 221 does not include salicide, but gate 251 may include salicide. In various embodiments, the gate dielectric (219/259) is silicon oxide. Other exemplary gate dielectrics include silicon nitride, silicon oxynitride, a dielectric with a high dielectric constant (high k), and/or combinations thereof. Examples of high k materials include hafnium silicate, hafnium oxide, zirconium oxide, aluminum oxide, tantalum pentoxide, hafnium dioxide-alumina ($Hf_{O2}$-$A_{l2O3}$) alloy, or combinations thereof. The FET may be formed using typical CMOS processes such as, photolithography; ion implantation; diffusion; deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer CVD (ALCVD), spin on coating; etching including wet etching, dry etching, and plasma etching; and/or other suitable CMOS processes.

Referring back to FIG. 1A, in block 104 a sacrificial plug is formed over a portion of the gate electrode for a subset of the FETs. The process for forming the sacrificial plug according to some embodiments is illustrated in flow chart format as FIG. 1B. In block 152 of FIG. 1B, a protective layer is deposited on the wafer over the gate structures. The protective layer may include one or many layers of different material. FIG. 2 includes protective layer 223 and 263 over the gate structures 211 and 251, respectively. The protective layer 223 and 263 are etch stop layers to ensure that the gate electrodes 221 and 261 are not damaged during plasma processing. In some embodiments, the protective layer is silicon oxynitride, carbon doped silicon oxynitride, carbon doped silicon oxide, or carbon doped silicon nitride. The protective layer has a thickness that ensures that the gate electrodes are protected. In one example, a silicon oxynitride protective layer may be about one thousand angstroms thick. The protective layer may be deposited directly on the gate electrode or indirectly, by depositing on an intermediate layer between the protective layer and the gate electrode. In some embodiments, a silicon oxide layer, for example, a silicon oxide layer formed using Tetraethyl orthosilicate (TEOS), is used between the protective layer and the gate electrode. The silicon oxide layer may be thinner than the protective layer, for example, 200 angstroms thick. According to various embodiments, the protective layer and the intermediate layer have different etch selectivities to the etch processes in the method embodiments of the present disclosure. The selections of the materials for the protective layer and the intermediate layer allows a soft landing etch on the gate electrode so little or no damage from the etch plasma results.

Figure 3:
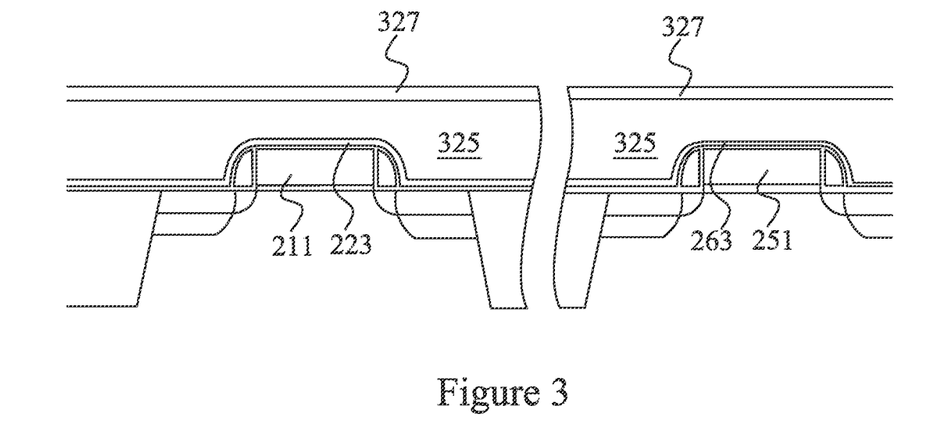

Referring to process 104 of FIG. 1B, in block 154, an inter-layer dielectric (ILD) is deposited over the FETs. The ILD may include one or more layers (e.g., ILD layer(s)) and may include silicon dioxide, fluorinated silicon glass (FGS), SILK (a product of Dow Chemical of Michigan), BLACK DIAMOND (a product of Applied Materials of Santa Clara, Calif.), and/or other insulating materials. The ILD may be formed by suitable processes typical in CMOS fabrication such as CVD, ALD, spin-on coating, and/or other processes. In some embodiments, the ILD includes two or more silicon oxide layers deposited using different processes. One example is an ILD having a Borophosphosilicate tetraethylorthosilicate (BPTEOS) layer and an undoped TEOS layer deposited using plasma. After the ILD layer(s) is deposited, the wafer may be planarized. One or more layers may be deposited after the ILD, including a bottom anti-reflective coating (BARC) layer. In FIG. 3, an ILD layer 325 and BARC 327 are disposed over protective layer 223/263 and the gate structures 211 and 251.

Figure 4A:
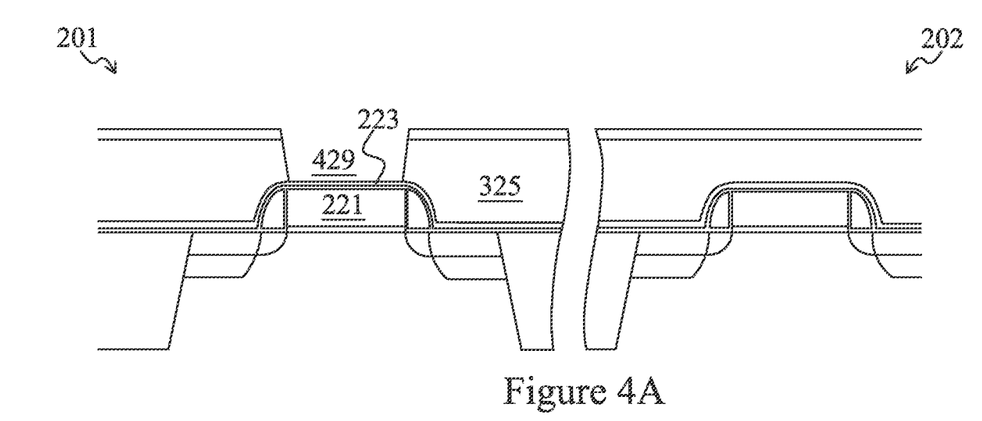
FIGS. 4A/4B to FIGS. 13A/13B are cross-sectional views of a BioFET device at various intermediate stages of formation according to one or more aspects of the present disclosure.
Figure 4B:
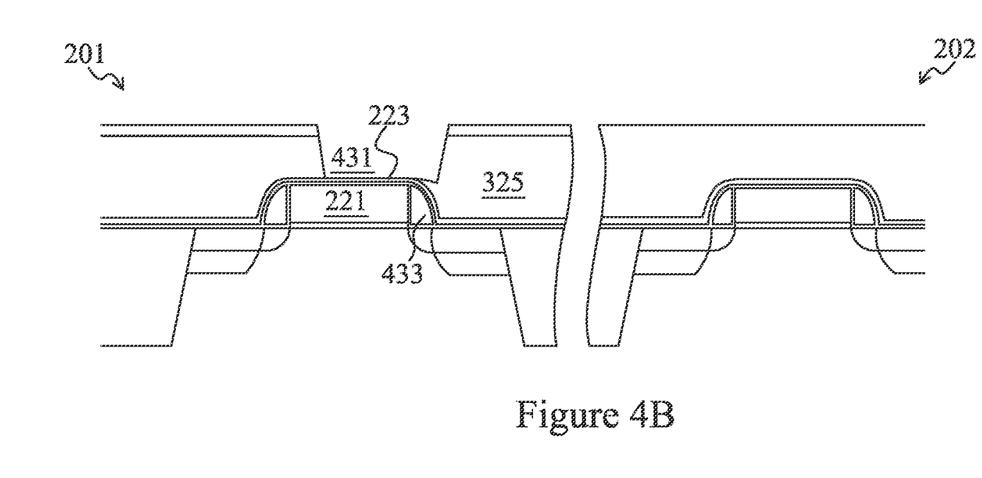

Referring to process 104 of FIG. 1B, in block 156, an opening is etched through the ILD to expose the protective layer for a subset of the FETs. The subset of the FETs refer to the BioFETs of the present disclosure. In FIGS. 4A and 4B, an opening 429 and 431 are shown in the BioFET 201. FIG. 4A shows an example of the process with good alignment. FIG. 4B shows an example where the opening 431 is not perfectly aligned with the gate structure. For the remainder of the Figures and discussion, all Figures having a "B" designation show the imperfect alignment example. The opening is formed by photolithography processes to pattern the opening followed by suitable wet, dry or plasma etching processes. Because the protective layer 223 is much harder to etch than the ILD 325, the use of the protective layer 223 ensures that a bottom of the openings 429 and 431 is the protective layer 223 and that the gate electrode 221 is not exposed even if the opening is aligned imperfectly, as shown in FIG. 4B. When the photolithography process misaligns without a protective layer 223, a portion of the spacer 433 may be exposed and etched. However, with the protective layer 223 of the present disclosure, even under misalignment conditions the spacer 433 is protected.

Figure 5A:
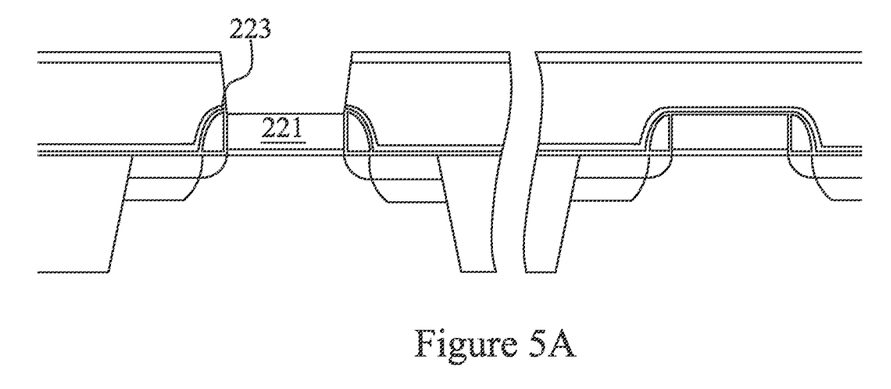
Figure 5B:
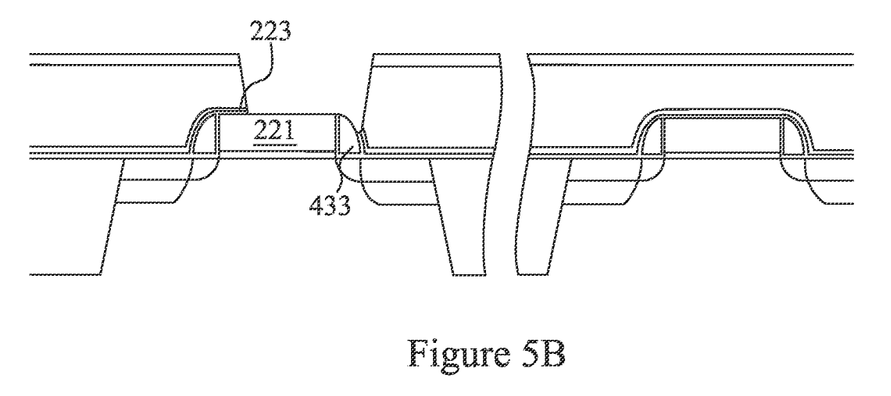

Referring to process 104 of FIG. 1B, in block 158, a soft landing etch is performed on the protective layer. A soft landing etch ensures that the underlying material is not removed unnecessarily. In some embodiments, the soft landing etch is performed using a dry etch process with little or no bias power and low energy plasma or no plasma and stops when an etch stop condition is detected. Process conditions during the etch is monitored and when a parameter changes corresponding to an etched material property change, the etch stop condition is detected. When used with a slow etch process, the end point detection can stop the etch accurately and minimized plasma-induced damage to the underlying material, for example, the gate electrode 221. FIGS. 5A and 5B are cross sectional views of the wafer after the soft landing etch. In FIG. 5A, the protective layer 223 above the gate electrode 221 is completely removed. In FIG. 5B, the protective layer 223 above a portion of the gate electrode 221 and the spacer 433 is removed.

Figure 6A:
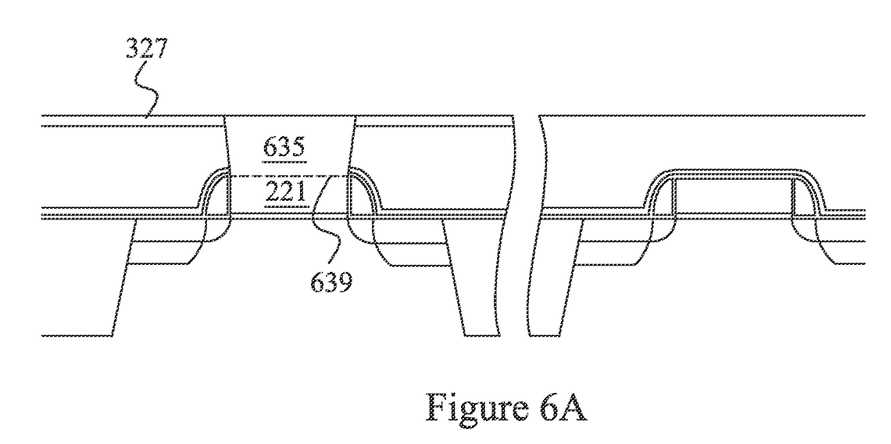
Figure 6B:
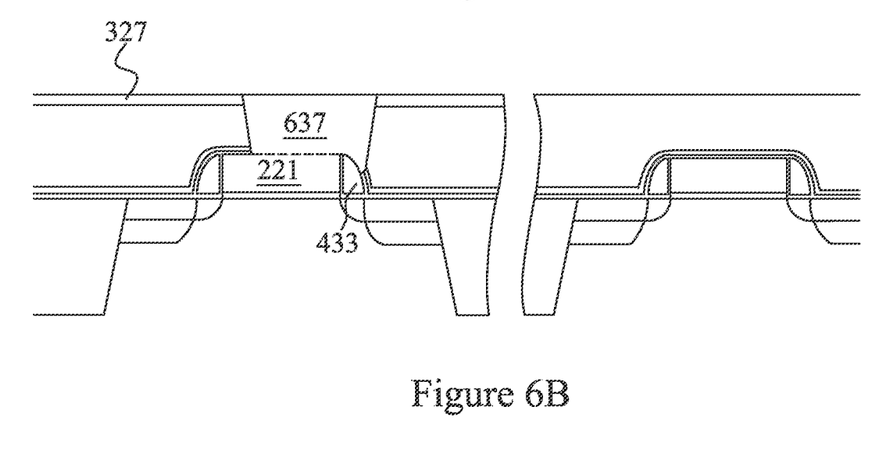

Referring to process 106 of FIG. 1B, in block 160, a sacrificial plug is deposited in the opening. According to various embodiments, the sacrificial plug is made of a same material as that of the gate electrodes 221, for example, polysilicon. However, the sacrificial plug may be another material that has sufficient etch selectivity difference as compared to overlying MLI layers to be deposited in subsequent operations. After the sacrificial plug is deposited, in block 162, the wafer is planarized to remove excessive sacrificial plug material. A chemical mechanical planarization (CMP) process may be used. FIGS. 6A and 6B are cross sectional views of the wafer after the planarization. In FIG. 6A, the wafer is planarized down to the BARC 327. The sacrificial plug 635 is disposed over the gate electrode 221. The dotted line 639 between the sacrificial plug 635 and the gate electrode 221 denotes an interface that may or may not exist and/or may not be detectable. When the sacrificial plug 635 and the gate electrode 221 are made of the same material and are formed under similar process conditions, no interface 639 exists. When different materials are used, an interface 639 exists. In some embodiments, a thin layer of silicon oxide, the intermediate layer between the protective layer and the gate electrode, separates the sacrificial plug 635 and the gate electrode 221. In these embodiments, the soft landing etch stops at the intermediate layer and not the gate electrode. FIG. 6B shows the sacrificial plug 637 disposed over a portion of the gate electrode 221 and a portion of the gate spacer 433. Process 104 as shown in FIG. 1B describes some embodiments of forming the sacrificial plugs 635 and 637, but other methods consistent with the CMOS process may be used. For example, the opening may be etched after one metal layer is formed instead of before. Depending on the material and deposition condition of the sacrificial plug, thermal budget considerations may limit the process sequence. In yet another example, the gate electrode and the sacrificial plug may be formed together during the gate formation process. Different gate sizes for the BioFET 201 and the non-Bio FET 202 may be achieved by etching the non-Bio FET gate.

In a plan view, the sacrificial plug may not extend to the entire length of the gate electrode. In various embodiments, a portion of the gate electrode remains in the BioFET to bias the transistor during operation in a similar capacity as a back gate.

Figure 7A:
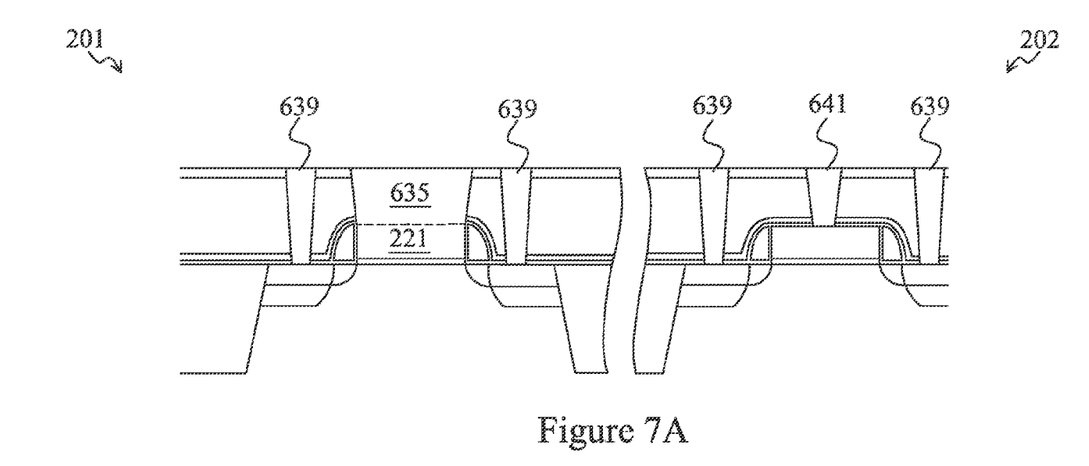
Figure 7B:
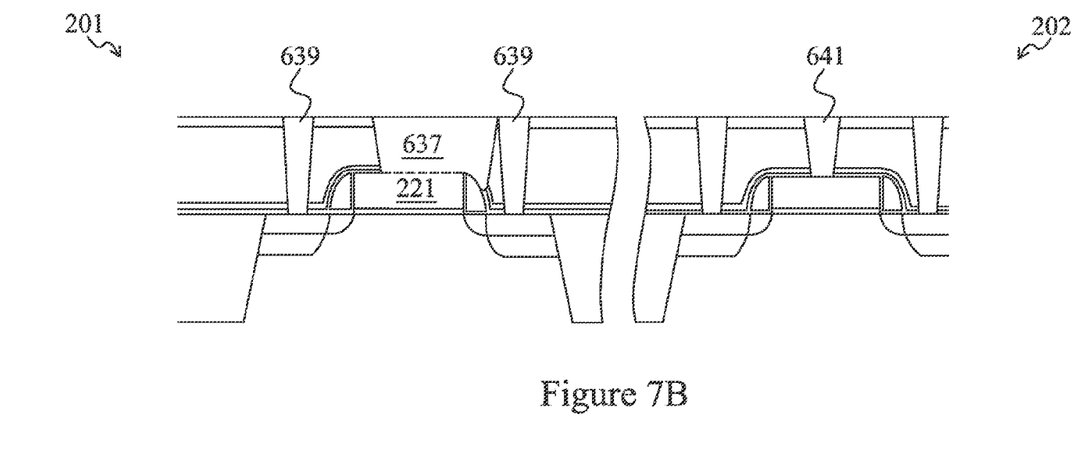

After the process 104 of forming the sacrificial plug, the process returns to FIG. 1A where in block 105 contacts are formed on the FETs. The contacts are formed in typical CMOS processing. FIGS. 7A and 7B shows contacts 639 formed over and physically connecting to the source/drain regions of the FETs 201 and 202 and contact 641 formed over and physically connecting to the gate electrode of FET 202. In some embodiments, contact 641 formed over and physically connecting to the gate electrode is also formed over BioFET 201, but in a different cross section not including the sacrificial plug 635 (637) and outside of the micro well to be formed in subsequent operations. In embodiments of BioFET 201 where the threshold voltage is sufficiently small, no contact is used. In FIG. 7B, the misaligned sacrificial plug 637 is physically close to but not touching the contact 639. If the misalignment is so severe that the sacrificial plug 637 makes contact with contact 637, then the BioFET 201 would be defective.

Referring back to FIG. 1A, in block 106 a multi-layer interconnect (MLI) is formed over the FETs. The MLI structure may include conductive lines, conductive vias, and/or interposing dielectric layers (e.g., interlayer dielectric (ILD)). The MLI structure provides electrical connection to the transistor. The conductive lines in various levels may comprise copper, aluminum, tungsten, tantalum, titanium, nickel, cobalt, metal silicide, metal nitride, poly silicon, combinations thereof, and/or other materials possibly including one or more layers or linings. The interposing or inter-layer dielectric layers (e.g., ILD layer(s)) may comprise silicon dioxide, fluorinated silicon glass (FSG), SILK (a product of Dow Chemical of Michigan), BLACK DIAMOND (a product of Applied Materials of Santa Clara, Calif.), and/or other insulating materials. The MLI may be formed by suitable processes typical in CMOS fabrication such as CVD, PVD, ALD, plating, spin-on coating, and/or other processes.

Figure 8A:
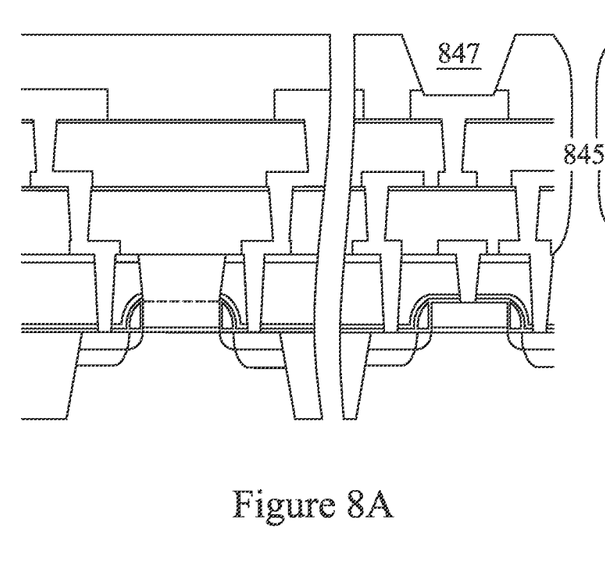
Figure 8B:
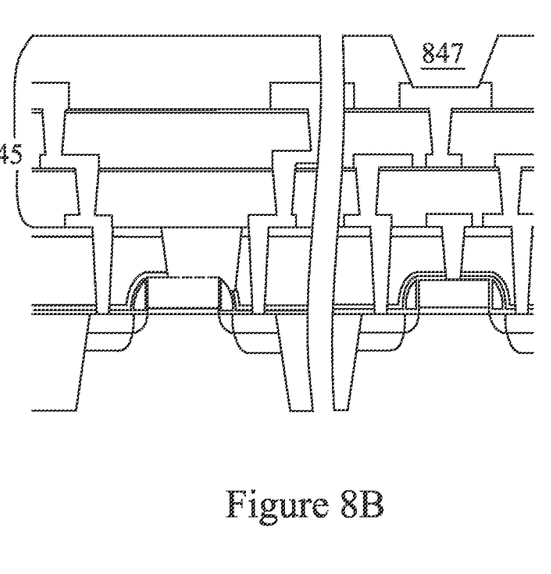

Referring to the example of FIGS. 8A and 8B, a MLI structure 845 is disposed on the wafer over the FETs and contacts. The MLI structure 845 includes a plurality of conductive lines connected by conductive vias or plugs. In various embodiments, the conductive lines include aluminum and/or copper. The vias include tungsten or copper. A dielectric layer is disposed between and interposing the conductive features of the MLI structure 845. The dielectric layer may be an ILD layer and/or composed of multiple ILD sub-layers. In various embodiments, the dielectric layer includes silicon oxide, silicon oxynitride, and/or silicon nitride. Openings 847 in a passivation layer above the topmost level of the MLI may be formed. During the device design, no conductive lines is routed over the BioFET to allow access to the sensing surface in a subsequent micro well etching operation.

The number of metal layers in the MLI depends on routing needs for the FETs. For simple BioFET devices where little or no analysis and processing are performed on the device, one or two metal layers are adequate. The non-Bio FETs merely perform little analysis and processing and output the results to another device. For complex BioFET devices where a significant amount of processing takes place, more metal layers are used, for example, four, five, or even eight metal layers. The use of more metal layers allows more non-BioFETs to be used on the device, which non-BioFETs that can perform complex logic operations with or without additional external input. Further, the results from the BioFETs can be used as an input that triggers further device operations. In one example, the further device operation may direct the contents of a micro well toward a more sensitive BioFET or a BioFET where a chemical reaction would break up some of the biological content. With additional processing power, a lab-on-a-chip type of device is formed where the output from the device includes results of the analysis instead of only raw data. For example, the device may determine whether a blood sample contains cancer cells, quantify the cancer cells, and output a cancer type. In another example, the device may determine a genetic sequence.

Figure 9A:
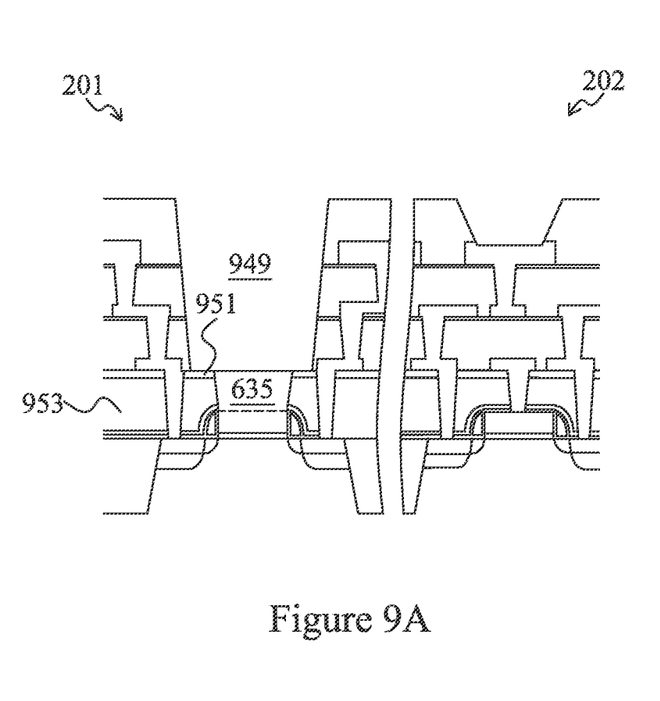
Figure 9B:
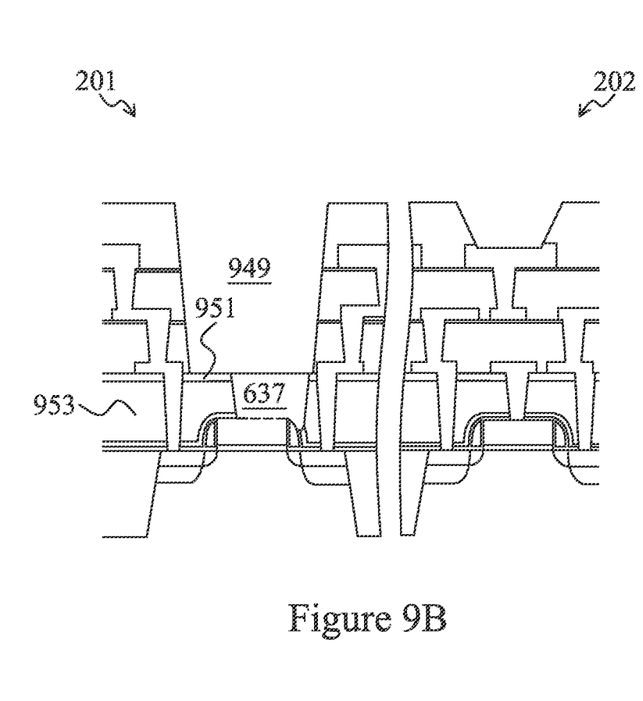

Referring back to FIG. 1A, in block 108 the MLI is etched to expose at least a portion of the sacrificial plug, thereby forming a portion of a micro well. Referring to FIGS. 9A and 9B, the etch process forms first well portion 949 of a micro well. The etch process is a deep oxide etch with plasma in the illustrated embodiment. The process is tuned to detect an etch end point at the silicon oxynitride layer 951 or sacrificial plug 635 material. The silicon oxynitride layer 951 may have been deposited over the ILD layer 953 before forming the sacrificial plugs 635 and 637 in some embodiments. Because the silicon oxynitride layer and sacrificial plugs are used, an aggressive plasma etch process may be used without damaging the gate. Subsequent to the first etch end-point, the silicon oxynitride layer 951 may be etched using a soft or slower etch process to reduce the likelihood of plasma induced damage.

When the entire micro well is etched only once, the process window of the deep oxide etch limits the aspect ratio of the opening and therefore the number of metal layers in the MLI. For example, an MLI may have 4 metal layers, along with a passivation layer and a gate width of 0.18 microns, the aspect ratio of the micro well may be over 30. Such high aspect ratio is very difficult, if not impossible, to etch, especially if care must be taken to avoid damaging the gate.

The micro well of the illustrated embodiments has at least two portions and may have three or more portions stacked on top of each other that are etched with a different process and/or geometry. According to various embodiments, aspect ratio of the first well portion is designed to fit within the process window of the deep oxide etch. With a multi-tiered micro well, the first well portion may still have the same number of metal layers; however, because the gate is protected, more aggressive process parameters may be used. In some embodiments, the micro well is etched in multiple steps where the first etch forms an opening for only a portion of the micro well, which decreases the aspect ratio of each etched opening. Upper portions may have a larger (wider) opening and bottoms than lower portions, allowing for an even smaller aspect ratio for upper portions. The first portion 949 of the micro well has an aspect ratio less than 20 in some embodiments, less than 15 in some embodiments, or even less than 10 in some embodiments. The use of a tiered micro well allows the total number of metal layers in the MLI to be four, six, eight, or even greater. A bottom of the first portion of the micro well may be at the sacrificial plug or at an intermediate level. The bottom areas of the various portions of the micro well are different, with larger bottom areas in upper portions and smaller bottom areas in lower portions. In some embodiments, a ridge is formed at the bottom of an upper portion, with an opening that is a top of a lower portion. Of course, the bottom-most portion exposes a sensing surface, which may be the gate electrode or the gate dielectric. The various portions have bottoms and tops that at least partially overlap.

After etching one or more times, at least a portion of the sacrificial plug is exposed. FIG. 9A is a cross section of a BioFET 201 and non-Bio FET 202 with an etched first portion 949 of a micro well. A bottom of the first portion 949 includes top of the sacrificial plug 635 and silicon oxynitride layer 951. FIG. 9B is a cross section of a BioFET 201 and non-Bio FET 202 where the sacrificial plug 637 is aligned imperfectly with the gate electrode. In some embodiments, only a portion of the top of the sacrificial plug 637 is exposed. In some embodiments, the silicon oxynitride layer 951 in FIGS. 9A and 9B are removed.

Referring back to FIG. 1A, in block 110 the sacrificial plug is removed using a non-plasma etch to form a second well portion or a bottom well portion of the micro well. A non-plasma etch process to remove polysilicon may expose the wafer to xenon fluoride ($XeF_2$) in a gaseous form. A wet etch process may include using potassium hydroxide (KOH), Tetramethylammonium hydroxide (TMAH) or Hydrofluoric Acid+Nitric Acid+Acetic Acid (HNA) as etchants. A non-plasma process ensures that no charge-induced damage results on the gate. The etching stops at the gate electrode if a dielectric interface layer is used between the sacrificial plug and the gate electrode. If no dielectric interface layer is used, then the etching can proceed to also remove the gate electrode in optional block 112. A part of the gate electrode not under the sacrificial plug would not be removed.

Figure 10A:
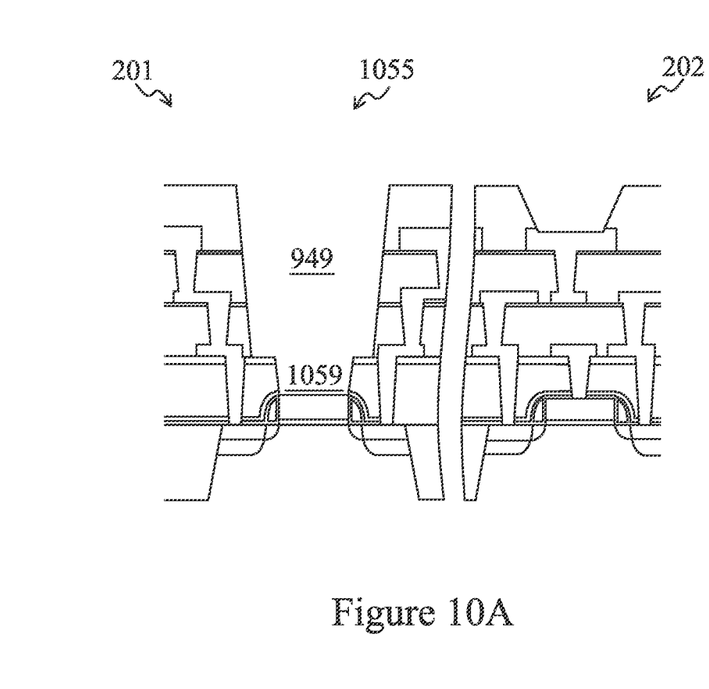
Figure 10B:
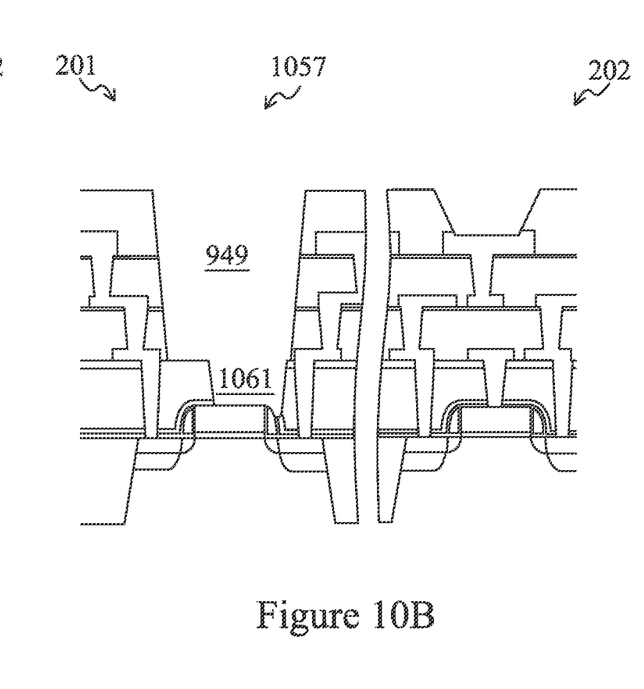

FIGS. 10A and 10B are cross section views of a partially fabricated BioFET 201 and non-Bio FET 202 after the sacrificial plug is removed. As shown, the micro well includes two portions, 949 and 1059 for micro well 1055 in FIG. 10A, and 949 and 1061 for micro well 1057 in FIG. 10B. In some embodiments, openings for micro wells 1055 and 1057 are completed at this stage. The ultimately to-be-formed bottom surface of micro wells 1055 and 1057 are sensing surfaces used to detect presence of target biomolecule. Further operations may include coating the bottom or the side surface of the micro well with different materials to aid sensing and analysis, as discussed further in association with blocks 118 and 120.

Figure 11A:
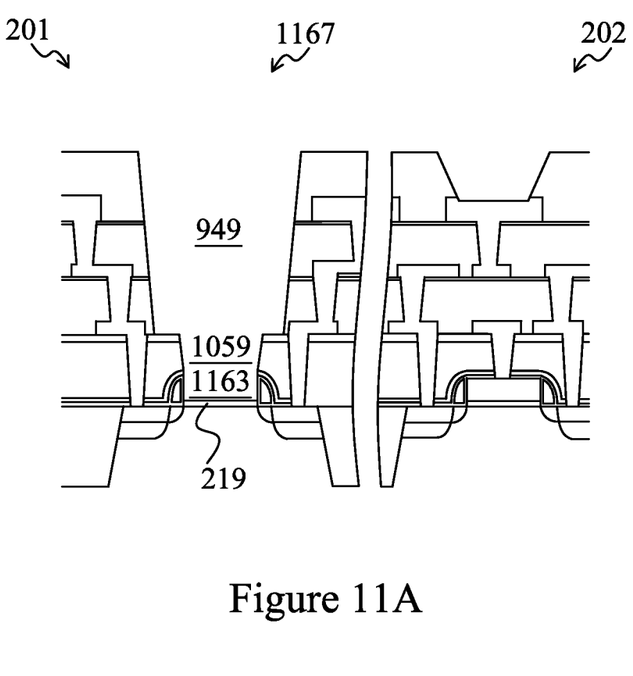
Figure 11B:
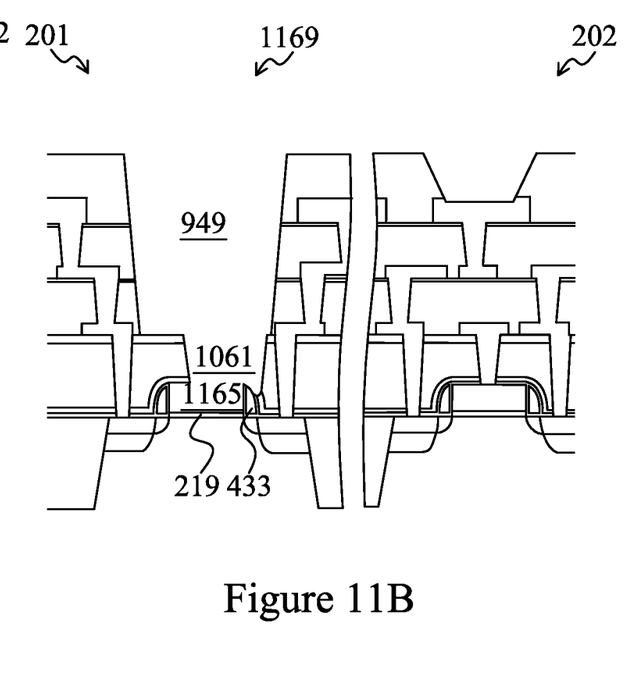

FIGS. 11A and 11B are cross section views of partially fabricated BioFET 201 and non-Bio FET 202 after the gate electrode is removed. Removing the gate electrode exposes the gate dielectric 219 that becomes the sensing surface. As shown in FIG. 11A, the micro well includes three portions, 949, 1059, and 1163 for micro well 1167. The portions 1059 and 1163 in micro well 1167 are perfectly aligned and thus do not include a difference in area or have a ridge between them. Thus portions 1059 and 1163 may be considered to be one portion of the micro well 1167. As shown in FIG. 11B, the micro well 1169 includes three portions, 949, 1061, and 1165. The portions 1061 and 1165 of micro well 1169 are not perfectly aligned and a ridge is formed over the spacer 433. The imperfect alignment in FIG. 11B does not affect the sensing surface above gate dielectric 219 of micro well 1169 because the isotropic etch used to form the portions 1061 and 1165 is strongly selective for polysilicon.

Figure 12A:
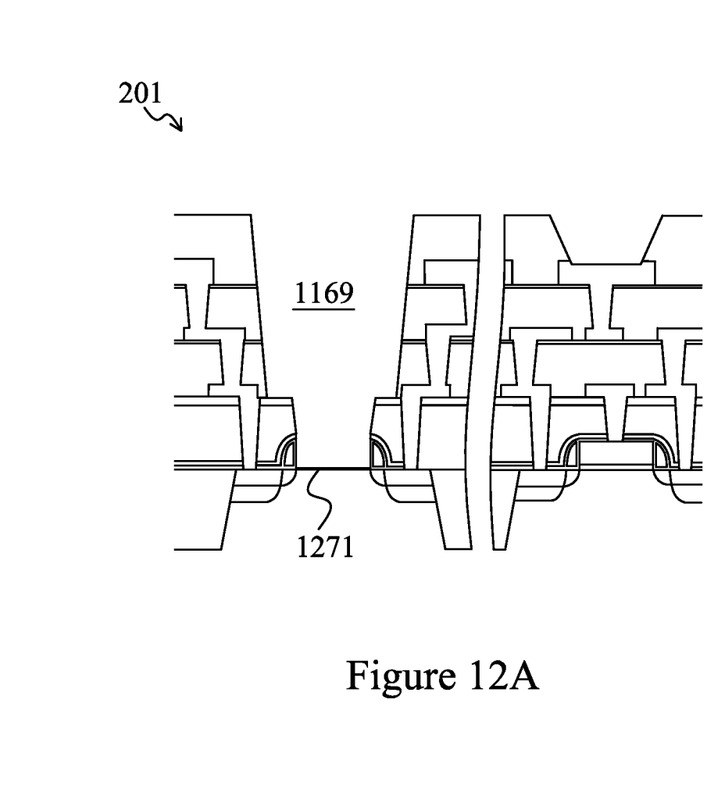
Figure 12B:
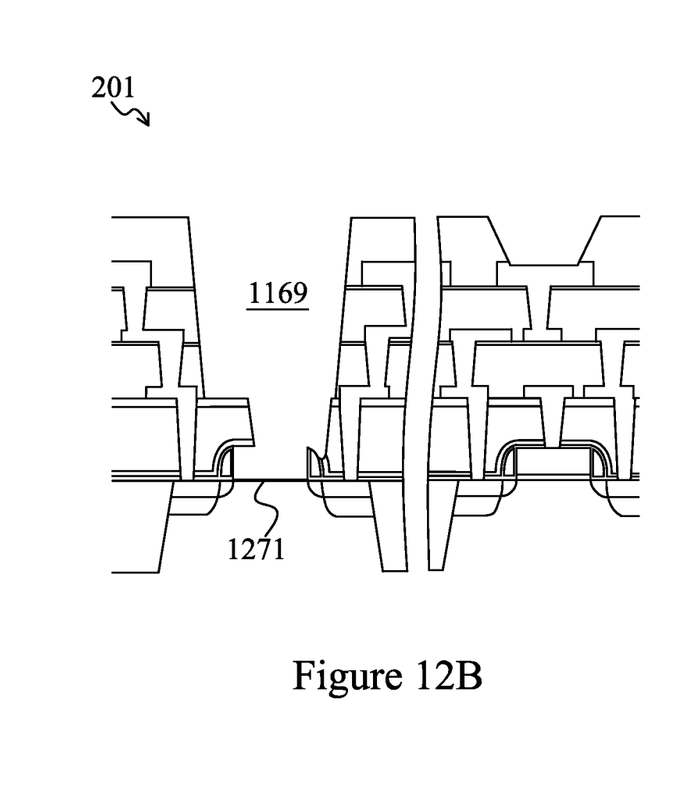

Referring back to FIG. 1A, in optional block 114 a portion of the gate dielectric is removed at the bottom of the micro well and replaced with a biological compatible high k dielectric in block 116. An original gate dielectric may be a silicon oxide ($SiO_2$). The replacement gate dielectric is a biological compatible high k dielectric such as silicon nitride ($Si_3N_4$), aluminum oxide ($Al_2O_3$), hafnium oxide ($HfO_2$), titanium oxide ($TiO_2$), or tantalum oxide ($Ta_2O_5$) that are more sensitive and can result in an increased gate capacitance and a lower threshold voltage for BioFET 201. Other high k dielectric includes hafnium silicate ( ), zirconium silicate ( ), zirconium oxide ( ), tin oxide (SnO or $SnO_2$), and BST (Barium Strontium Titanate) ($Ba_xSr_{1-x}TiO_3$). BST is a very high dielectric constant material that can potentially provide a very sensitive sensing surface. The high k dielectric may be deposited using atomic layer deposition (ALD) or other CVD techniques. When the high k dielectric is deposited, within the micro well, deposition on the sidewalls away from the sensing surface may not be removed. FIGS. 12A and 12B are cross section views of a partially fabricated BioFET 201 and non-BioFET 202 after the deposition of a replacement gate dielectric 1271 at the bottom of the micro well 1169.

Referring back to FIG. 1A, in optional block 118 a sidewall of the micro well is coated with a first coating. The first coating lines the sides of the micro well, which in some embodiments functions as a fluidic channel. In some embodiments, the first coating protects the ILD and any metal exposed during the deep oxide etch from the fluid to be analyzed during the BioFET operation. In some embodiments, the first coating also aids the analysis by preventing unwanted accumulation and deposition of target biomolecules to be analyzed. For example, the first coating may be a polytetrafluoroethylene (PTFE) material such as Teflon®, available from DuPont Company of Wilmington, Del. In another example, the first coating may be a surfactant. Depending on the fluid, the first coating may have a hydrophobic or hydrophilic surface that prevents unwanted accumulation of target biomolecules. In one example, the first coating may include a self-assembled monolayer of a surfactant molecule to be exposed to the fluid. In some embodiments, the first coating includes material that aid in the movement of the fluid. For example, the first coating may include magnetic material or ferromagnetic material for magnetophoresis, metals for electrophoresis, or a particular dielectric material for dielectrophoresis. The first coating material for aiding movement of the fluid may be deposited in a pattern that varies in the direction of the fluid flow.

Figure 13A:
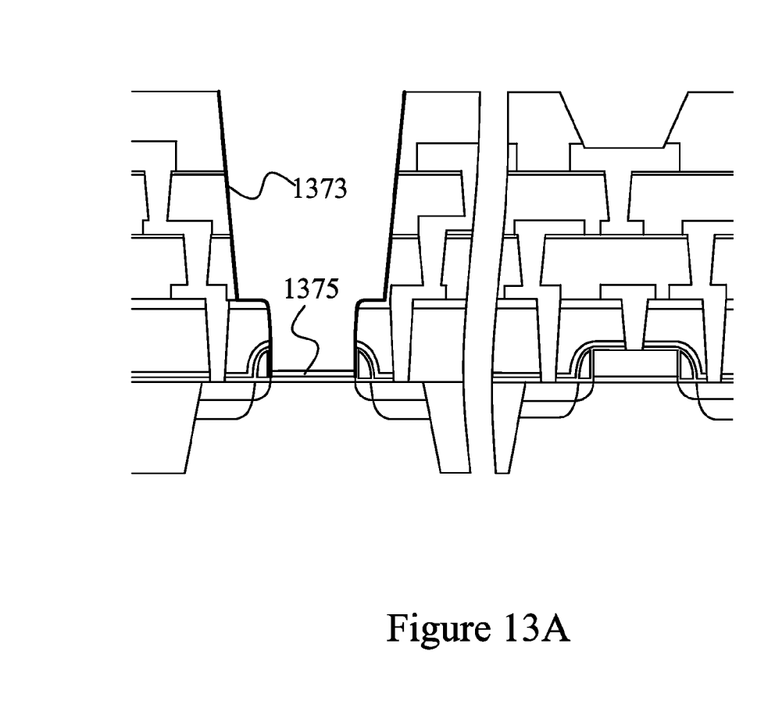
Figure 13B:
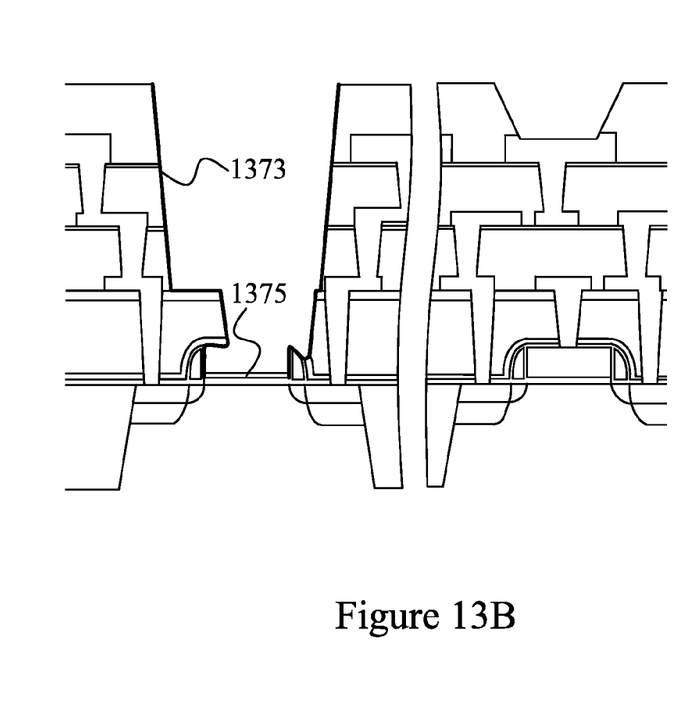

In optional block 120, a bottom of the micro well is coated with a second coating. According to various embodiments, the second coating is different from the first coating. The second coating includes receptors that can bind to the target biomolecule or include material that can be bound to a receptor. A receptor may be an enzyme, antibody, ligand, peptide, nucleotide, cell of an organ, organism or piece of tissue. In some embodiments, the second coating has a hydrophilic surface. The second coating may include a self-assembled monolayer of molecules. FIGS. 13A and 13B are cross section views of a partially fabricated BioFET 201 and non-BioFET 202 after the coating of first coating 1373 and second coating 1375. Depending on the method used to apply the coating, the irregular surface from the imperfect alignment shown in FIG. 13B may be compensated or overcome. For example, an isotropic application may be used to apply the first coat, and then an anisotropic application may be used to apply the second coat. In some embodiments, only the first coating or only the second coating is provided. In some applications, more than one coating may be applied to different portions. For example, for the sensing surface, a binding coat may be applied as a surface preparation to provide binding sites, and in some instances a bio-entities coat may include bio-entities that can detect a target biomolecule.

After the process 100 of FIG. 1A, the CMOS process proceeds to form bond pads for packaging the BioFET. The BioFET device may include additional passive components such as resistors, capacitors, inductors, and/or fuses; and other active components, including P-channel field effect transistors (PFETs), N-channel field effect transistors (NFETs), metal-oxide-semiconductor field effect transistors (MOSFETs), complementary metal-oxide-semiconductor (CMOS) transistors, high voltage transistors, and/or high frequency transistors; other suitable components; and/or combinations thereof. It is further understood that additional features can be added in the BioFET device, and some of the features described below can be replaced or eliminated, for additional embodiments of the BioFET device.

The BioFET may include additional fluidic channels and enclosures. The fluidic channels may provide a channel or container (e.g., reservoir) operable to hold and/or direct a fluid. In some embodiments, the fluidic channel includes polydimethylsiloxane (PDMS) elastomer. However, other materials may be used. The fluidic channel may be fabricated and/or connected or bonded to the BioFET device outside of a CMOS process, for example, the fluidic channel may be fabricated and/or connected to the device using processes that are not typical of standard CMOS fabrication. In an embodiment a second entity, separate from the entity fabricating the transistors, may connect the fluidic channel to the BioFET device. The fluid being utilized may be a chemical solution. The fluid may contain target biomolecules or bio-entities.

The BioFET device may include sense amplifiers that can enhance the signal quality and magnification to improve the detection ability of the BioFET device. According to various embodiments, when the gate of the BioFET is triggered by the bio-molecule presence, the BioFET will transfer electrons and induce the field effect charging of the device, thereby modulating a current (e.g., Ids). The change of the current (e.g., Ids) or threshold voltage (Vt) can serve to indicate detection of the relevant biomolecules or bio-entities. Thus, the device can achieve a biosensor application including application with differential sensing for enhanced sensitivity.

In some embodiment, a CMOS fabrication facility (e.g., foundry) may process the method 100 of FIG. 1A and/or the associated device up to the fluidic channel formation. A subsequent user may provide the surface treatment technologies, ionic solutions, receptors, and the like. In summary, the methods and devices disclosed herein provide a BioFET that is fabricated using CMOS and/or CMOS compatible processes. Some embodiments of the disclosed BioFET may be used in biological and/or medical applications, including those involving liquids, biological entities, and/or reagents. One detection mechanism of some embodiments described herein includes a conductance modulation of the FET of the BioFET due to the binding of the target bio-molecule or bio-entity to the gate structure, or a receptor molecule disposed (e.g., immobilized) on the gate structure of a device.

One aspect of the present disclosure pertains to a biological field-effect transistor (BioFET) device that includes a substrate and BioFETs. Each BioFET includes a micro well having a top well portion and a bottom well portion, wherein a bottom surface area of the top well portion is different from a top surface area of the bottom well portion, and a gate dielectric on the substrate below a bottom surface of the bottom well portion. Another aspect of the present disclosure pertains to a device, which may be an integrated circuit chip that includes a substrate having a biological field-effect transistor (BioFET) region and a complementary metal-oxide semiconductor field-effect transistor (C-MOSFET) region. BioFETs in the BioFET region include a micro well having a plurality of stacked well portions and may include a ridge between adjacent well portions, and a gate dielectric on the substrate below a bottom surface of the micro well. A multi-layer interconnect (MLI) surrounds the micro well of the BioFETs.

In yet another aspect, the present disclosure pertains to a method of making a BioFET device. The method includes forming FETs on a semiconductor substrate, forming a sacrificial plug over a portion of the gate electrode for a subset of the FETs, forming contacts and a multi-layer interconnect (MLI) over the FETs, etching the MLI to expose at least a portion of the sacrificial plug, and removing the sacrificial plug using a non-plasma etch to form a second well portion of the micro well. The FETs include a gate structure formed on a first surface of the semiconductor substrate and a channel region.

In describing one or more of these embodiments, the present disclosure may offer several advantages over prior art devices. In the discussion of the advantages or benefits that follows it should be noted that these benefits and/or results may be present is some embodiments, but are not required in every embodiment. Further, it is understood that different embodiments disclosed herein offer different features and advantages, and that various changes, substitutions and alterations may be made without departing from the spirit and scope of the present disclosure.

What is claimed is:

1. A biological field-effect transistor (BioFET) device, comprising:
    a substrate;
    a plurality of BioFETs formed on the substrate, each BioFET comprising
    a micro well structure having a top well portion and a bottom well portion, wherein a bottom surface area of the top well portion is different from a top surface area of the bottom well portion,
    a source region adjacent a first side of the micro well structure and a drain region adjacent an opposite side of the micro well structure and a channel region extending below the micro well structure, and
    a dielectric on the substrate at a bottom surface of the bottom well portion.

2. The BioFET device of claim 1, wherein each micro well further has a middle well portion and wherein a top surface area of the middle well portion is different from the bottom surface area of the top well portion and a bottom surface area of the middle well portion is different from a top surface area of the bottom well portion.

3. The BioFET device of claim 1, wherein the dielectric is selected from the group consisting of $SiO_2$, $Si_3N_4$, $Al_2O_3$, $TiO_2$, $HfO_2$, $Ta_2O_5$, $SnO$, $SnO_2$, $Ba_xSr_{1-x}TiO_3$ and combinations thereof.

4. The BioFET device of claim 1, wherein each BioFET further comprises an electrode on the dielectric.

5. The BioFET device of claim 1, further comprising:
    a multi-layer interconnect (MLI) surrounding at least one micro well of the plurality of BioFETs, wherein the MLI has three or more metal layers.

6. The BioFET device of claim 1, further comprising logic processors, control circuits, signal amplifiers and A/D converters formed on the substrate.

7. The BioFET device of claim 1, further comprising:
    a fluidic channel between respective ones of the plurality of BioFETs.

8. The BioFET device of claim 1, wherein each BioFET further comprises:
    a coating on sidewalls of the micro well.

9. The BioFET device of claim 1, further comprising:
    a plurality of second BioFETs, each second BioFET comprising
    a micro well having a top well portion and a bottom well portion, wherein a bottom surface area of the top well portion is different from a top surface area of the bottom well portion, and
    an electrode and a dielectric on the substrate at a bottom surface of the bottom well portion.

10. The BioFET device of claim 1 wherein the BioFET further comprises:
    a gate electrode adjacent to the micro well.

11. A device, comprising:
    a substrate having a biological field-effect transistor (BioFET) region and a complementary metal-oxide semiconductor field-effect transistor (C-MOSFET) region;
    a plurality of BioFETs in the BioFET region, each BioFET comprising
    a micro well having a plurality of stacked well portions and a ridge between adjacent well portions;
    a gate dielectric on the substrate below a bottom surface of the micro well;
    a plurality of C-MOSFETs in the C-MOSFET region and,
    a multi-layer interconnect (MLI) comprising at least two vertically stacked layers of metal interconnects surrounding the micro well of the plurality of BioFETs.

12. The device of claim 11, wherein each BioFET further comprises a gate electrode on the gate dielectric.

13. The device of claim 11, wherein the gate dielectric is silicon nitride, hafnium oxide, or tantalum oxide.

14. The device of claim 11, further comprising:
    a coating on a bottom of the micro well.

* * * * *